United States Patent
Hammar et al.

(10) Patent No.: US 8,949,067 B1
(45) Date of Patent: Feb. 3, 2015

(54) DEVICE AND METHOD FOR MEASURING MATERIAL VOLUME CHANGES

(75) Inventors: Jarod Hammar, Cypress, TX (US); John D Norwood, Houston, TX (US)

(73) Assignee: OFI Testing Equipment, Inc., Houston, TX (US)

( * ) Notice: Subject to any disclaimer, the term of this patent is extended or adjusted under 35 U.S.C. 154(b) by 398 days.

(21) Appl. No.: 13/235,002

(22) Filed: Sep. 16, 2011

Related U.S. Application Data

(60) Provisional application No. 61/383,836, filed on Sep. 17, 2010.

(51) Int. Cl.
*G01C 9/00* (2006.01)

(52) U.S. Cl.
USPC .......................................................... 702/150

(58) Field of Classification Search
USPC ............................................ 702/150; 342/22
See application file for complete search history.

(56) References Cited

U.S. PATENT DOCUMENTS

| | | | | |
|---|---|---|---|---|
| 6,112,599 | A * | 9/2000 | Maki, Jr. | 73/801 |
| 6,817,238 | B2 * | 11/2004 | Go Boncan et al. | 73/149 |
| 6,918,292 | B2 * | 7/2005 | Go Boncan et al. | 73/149 |
| 7,240,545 | B1 * | 7/2007 | Jennings | 73/149 |
| 7,380,466 | B2 * | 6/2008 | Deeg | 73/803 |
| 8,156,798 | B1 * | 4/2012 | Bi | 73/149 |
| 2006/0102455 | A1 * | 5/2006 | Chiang et al. | 200/181 |
| 2007/0044572 | A1 * | 3/2007 | Davis et al. | 73/861.42 |
| 2007/0056383 | A1 * | 3/2007 | Deeg | 73/788 |
| 2007/0137285 | A1 * | 6/2007 | Jennings | 73/53.01 |
| 2011/0094295 | A1 * | 4/2011 | Meadows et al. | 73/38 |
| 2012/0072133 | A1 * | 3/2012 | Norwood et al. | 702/45 |
| 2012/0148452 | A1 * | 6/2012 | Brown et al. | 422/86 |

OTHER PUBLICATIONS

Chandler Engineering, Model 4268 ES Cement Expansion/Shrinkage Cell Brochure, 2008, http://www.chandlerengineering.com/Products/OilWellCementing/Model4268.aspx.
Keyence Corporation, Model LK-G407 CCD laser displacement sensor.

* cited by examiner

*Primary Examiner* — Sujoy Kundu
*Assistant Examiner* — Alvaro Fortich
(74) *Attorney, Agent, or Firm* — Keeling Patents & Trademarks, LLC; Kenneth A. Keeling; Mark S. Solomon

(57) ABSTRACT

A test cell for determining expansion or contraction of a sample contained therein includes, a test cell body, a reflective surface within the test cell body, the reflective surface moveable responsive to expansion or contraction of the sample, a displacement sensor system exterior of the cell body, the displacement sensor system having a transmitter for transmitting directed electromagnetic radiation and a sensor for sensing electromagnetic radiation, a lens provided in the cell body, the lens constructed to allow electromagnetic radiation to pass therethrough. The transmitter, reflective surface, and sensor are constructed and positioned such that directed electromagnetic radiation transmitted from transmitter toward reflective surface is reflected from reflective surface toward the sensor. In an exemplary embodiment, the lens is provided in a cell upper plug, with the translating member positioned for linear displacement toward and away from the lens responsive to expansion and contraction of a material sample.

20 Claims, 4 Drawing Sheets

DEVICE AND METHOD FOR MEASURING MATERIAL VOLUME CHANGES

CROSS-REFERENCE TO RELATED APPLICATIONS

This application claims the benefit of U.S. Provisional application Ser. No. 61/383,836, entitled "Device and Method for Measuring Material Volume Changes," filed Sep. 17, 2010, which application is incorporated herein by reference as if reproduced in full below.

STATEMENT REGARDING FEDERAL SPONSORED RESEARCH OR DEVELOPMENT

Not applicable.

FIELD OF THE DISCLOSURE

This invention relates generally to instrument test cells for measuring properties of materials, and more specifically, to a displacement measurement device and a test cell for determining volumetric expansion and contraction of materials within a controlled high-pressure, high-temperature environment.

BACKGROUND

In the oil and gas industry, it is beneficial to know pertinent properties of materials encountered down hole whether during initial drilling or thereafter. Well drilling and operation processes often require specifically formulated compositions, including cements and other compositions. It is beneficial to know how materials, cements and other compositions are affected by temperature, pressure, and time. Test cells are used for measuring volumetric expansion and shrinkage of materials including shale, cements, drilling fluids, and other material samples under high pressure and high temperature conditions similar to those found in a downhole environment.

A conventional test cell for measuring expansion and contraction of cement compositions uses a linear variable differential transformer, LVDT, to determine expansion or contraction of materials in a test cell. A magnetic core translates within an array of electrical coils. The translation of the magnetic core produces an electrical differential between the coils indicating the location of the core. Such differential is quantified to determine volume change.

An expansion/shrinkage cell is disclosed in U.S. Pat. No. 6,918,292 issued to Boncan and Bray in 2005. The cell is comprised of a mold having two wall sections attached to each other using springs and seals that allow a limited degree of expansion and contraction. One of the wall sections is attached to a base, while the other is left free to move with the expansion or contraction of the sample material. A cement sample is placed in the mold and allowed to cure. A linear displacement transducer measures the movement of the first and second wall sections relative to one another in response to volumetric changes in the cement.

U.S. Pat. No. 7,240,545 issued to Jennings in 2007 discloses a cement expansion and shrinkage cell that employs a moveable piston rod, which separates two chambers, to measure expansion and contraction. A digital measuring device, such as a linear variable differential transformer, is connected to the piston to measure linear movement of the piston as the sample expands or contracts.

Chandler Engineering markets a cement analyzer identified as Model 4268ES Cement Expansion & Shrinkage Option. The system measures change in volume of a cement sample using a diaphragm and displacement piston combined with a linear variable differential transformer.

As can be determined from the above prior art, test cells have traditionally used linear variable differential transformers to measure the volumetric change in the sample. However, this type of sensor has several disadvantages. To function, LVDTs require that the magnetic core be physically attached to the device that moves inside the pressurized test cell with the expansion or contraction of the sample material. Furthermore, the magnetic coil must be able to slide freely inside the test cell with coming into contact with it. This puts major constraints on the configurations of test cells using this type of sensor. Additionally, this type of sensor may be affected by external electromagnetic disturbances and has limited range and precision.

BRIEF SUMMARY OF THE DISCLOSURE

A device for measuring material volume changes includes a cell body, a translating member, a directed electromagnetic signal generator, a sensor, and a lens allowing transmission of a generated signal and a reflected signal. The cell body and the translating member create an upper chamber and a lower chamber. The lower chamber contains a sample material. The upper chamber is filled with a pressurizing media. As pressure is applied to the pressurizing media, the pressure in each chamber equalizes while maintaining at least partial separation of the sample material and the pressurizing media. The translating member has a reflective surface and a distal sample contact surface. The translating member translates responsive to expansion or contraction of a sample material. The directed electromagnetic signal generator, sensor, lens and reflective surface of the translating member are structured and positioned to allow a signal generated by the signal generator to pass through the cell body, encounter the translating member reflective surface and be reflected through the lens to the sensor. In an exemplary embodiment, the lens is provided in a cell upper plug, with the translating member positioned for linear displacement toward and away from the lens responsive to expansion and contraction of a material sample. The translating member is limited to axial linear movement by means of a cylindrical outer guide surface.

BRIEF DESCRIPTION OF THE DRAWINGS

For a more complete understanding of the exemplary embodiments of the invention, reference is now made to the following Description of Embodiments of the Invention, taken in conjunction with the accompanying drawings, in which.

DETAILED DESCRIPTION OF EMBODIMENTS OF THE INVENTION

Figure 1:
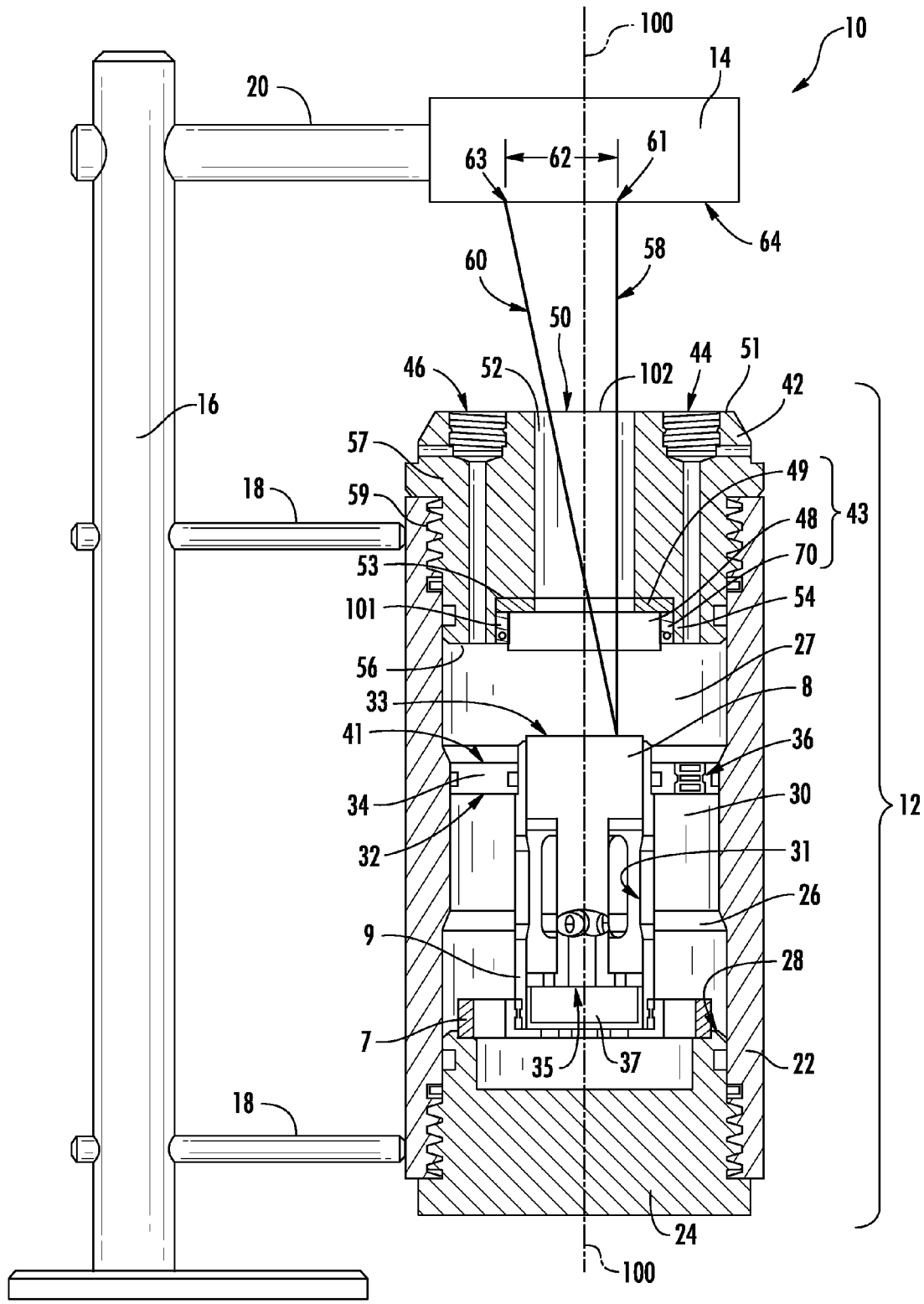
FIG. 1 is a partial cross-sectional view of a material expansion and shrinkage measurement cell apparatus.

The exemplary embodiments are best understood by referring to the drawings, like numerals being used for like and corresponding parts of the various drawings. The directions "lower" and "upper" as used in this specification are used for descriptive purposes only and it will be understood by one having skill in the art that different orientations are possible.

Figure 3:
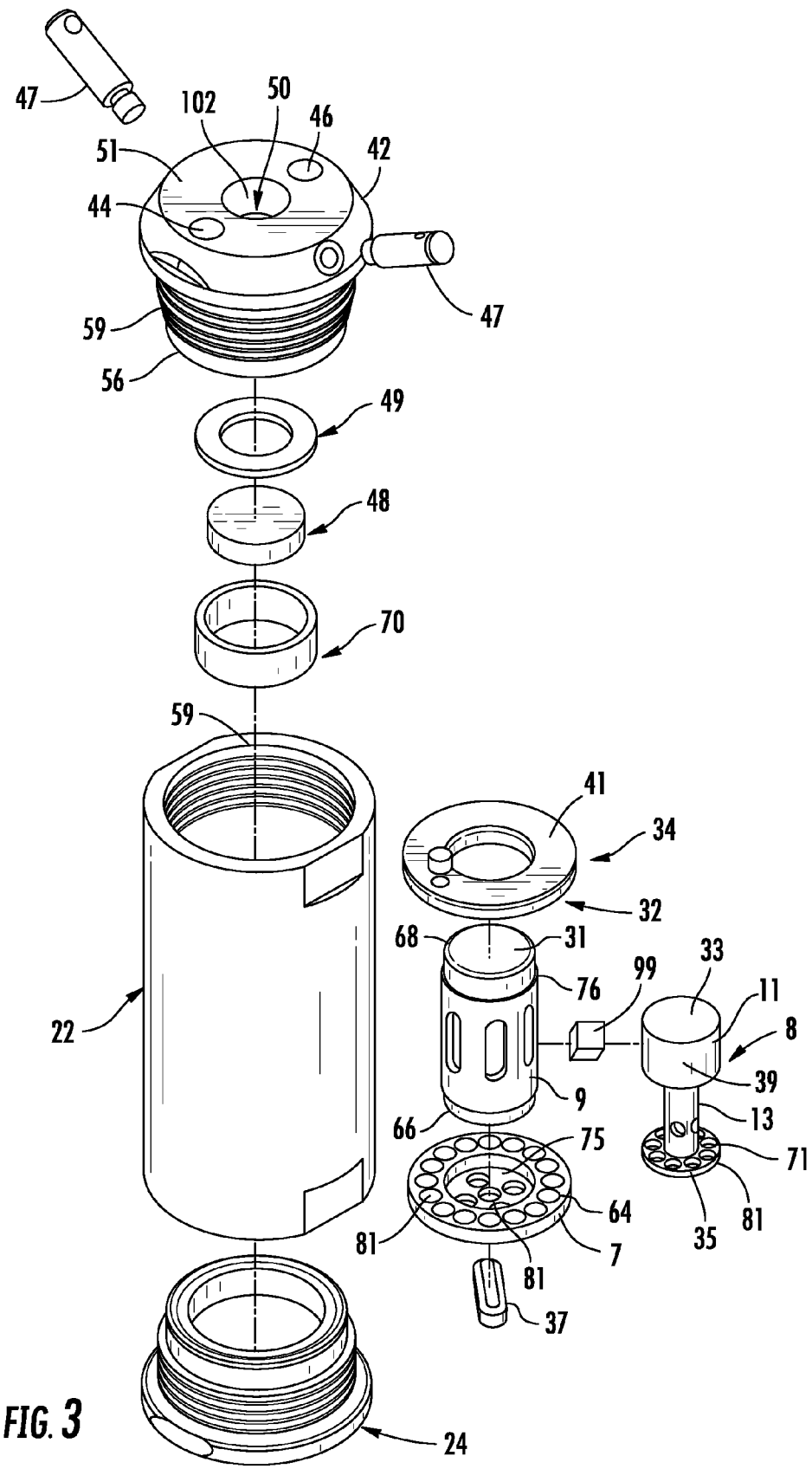
FIG. 3 is an exploded view of a material expansion and shrinkage measurement cell apparatus.

Referring to FIGS. 1 and 3, a test cell with a directed electromagnetic radiation measuring sensor apparatus 10 for measuring material expansion and shrinkage includes generally a cell 12 and a displacement sensor system 14. The cell 12 and the displacement sensor system 14 are held in their relative positions by stand 16. Stand 16 has lower arms 18 for supporting cell 12, and an upper arm 20 for supporting displacement sensor system 14. In an alternative embodiment, displacement sensor system 14 may be directly coupled to cell 12 instead of utilizing stand 16.

Cell 12 includes a hollow, cylindrical cell body 22, a lower plug 24, and an upper plug 42. Cell body 22 defines a central axis 100. Cell 12 is a vessel that may accommodate relatively high temperature and high pressure. An exemplary temperature range is atmospheric temperature up to 500 deg. F (260 deg. C). An exemplary pressure range is atmospheric pressure up to 10,000 psi (69 MPa).

Lower plug 24 is removably attached to a lower end of cell body 22. Upper plug 42 is attached to an upper end of cell body 22. In an exemplary embodiment lower plug 24 and upper plug 42 are threadably coupled to cell body 22.

Upper plug 42 includes openings defining a center bore 50 having a countersunk lower open section 54, a port 44, and a port 46. Port 44 is sized and structured to allow connection or insertion of a temperature-sensing element (not shown), such as a thermocouple, to facilitate temperature measurement. Port 46 is sized and structured to connect to a fluid source to allow ingress and egress of a pressurizing fluid to facilitate pressurization, de-pressurization, and pressure measurement. Center bore 50 is sized and structured to receive a lens assembly 43. Removable handles 47, depicted in FIG. 3, allow leverage to grip upper plug 42 during connection and release of upper plug 42 to cell body 22.

A sample holder 9 is positioned in cell 12 proximate lower plug 24. Sample holder 9 is a hollow, cylindrical structure. A sample holder base 7 includes a plate 75 with a counter-sunk opening defining a rim 64. Lower end 66 of sample holder 9 is positioned above plate 75 within rim 64.

A separator 34 is provided proximate upper end 68. Separator 34 comprises a ring structure sized and constructed to receive upper end 68 of sample holder 9. A shoulder 76 formed in sample holder 9 proximate upper end 68 abuts lower surface 32 of separator 34. In an assembled orientation, sample holder base 7 and separator 34 maintain sample holder 9 in a fixed orientation within cell body 22 with a central axis of sample holder 9 coaxial with axis 100.

A transfer stand 8 slidably fits within inner surface 31 of sample holder 9. Transfer stand 8 includes an upper head 11 a lower contact flange 35 and a rod 13 intermediate head 11 and flange 35. Exterior side surface 39 of head 11 is sized and structured to slide within interior surface 31 of sample holder 9. Exterior side surface 71 of flange 35 is sized and structured to slide within interior surface 31 of sample holder 9. Each of head 11 and flange 35 are coaxially aligned with axis 100. Accordingly, movement of transfer stand 8 within sample holder 9 is along axis 100.

Sample holder 9 and transfer stand 8 are constructed to allow placement of a material sample 99 within sample holder 9 on plate 75 with flange 35 resting on sample 99. Accordingly, expansion or contraction of sample 99 results in linear movement of transfer stand 8 along axis 100. Sample 99 may be any material desired to be tested including compounds, composites, and naturally-occurring materials. Sample 99 may be a fluid in a container (not shown) constructed to allow expansion or contraction of at least one surface.

Upper plug 42 comprises a hollow cylinder structure having an at least partially enclosed upper end 51 and an opposite lower end 56. Plug 42 includes a cylindrical wall 57 that defines interior center bore 50 and interior lower open section 54. Threading 59 is provided on the exterior of wall 57 for threading attachment of plug 42 by means of corresponding threading 59 to interior wall of cell body 22. Center bore 50 defines a centrally-oriented opening 102 in upper end 51. Center bore 50 includes an inner surface 52. Interior lower open section 54 terminates in an opening 101 proximate lower end 56. Interior open section 54 is a countersunk opening larger than center bore 50 defining shoulder 53 in wall 57. Shoulder 53 extends around the periphery of center bore 50.

Lens assembly 43 includes lens 48, spacer 49 and seal 70. Lens assembly 43 is sized and structured to fit within lower open section 54 of upper plug 43. Lens 48 is constructed of a material to allow directed electromagnetic radiation generated by the displacement sensor system 14 to pass through. If the electromagnetic radiation is visible light, lens 48 will be constructed to be transparent.

Referring to FIG. 1, a spacer 49 is positioned intermediate shoulder 53 and lens 48 of lens assembly 43. A seal 70 is positioned around lens 48 in the annulus between the side surface of lens 48 and the interior wall of lower open section 54. Seal 70 functions to prevent or substantially reduce fluid flow past lens assembly 43 into bore 50.

Lens 48 is oriented substantially parallel to upper surface 33 of transfer stand 8. Lens 48 allows transmission of electromagnetic radiation therethrough. The directed electromagnetic radiation may be generated by light amplification by stimulated emission of radiation ("LASER") and may include infrared, human-visible or other wavelengths or frequencies of radiation. Exemplary materials for lens 48 in exemplary embodiments include sapphire crystal, glass, quartz, plastics, and combinations thereof constructed to withstand temperature and pressure conditions of test cell 12.

Upper surface 33 of transfer stand 8 is constructed to reflect the directed electromagnetic radiation generated by transmitter 61 of displacement sensor system 14.

As separator 34 extends from sample holder 9 to the inner wall surface 30 of cell body 22, separator 34, cooperatively with head 11 separates the interior of cell 22 into an upper chamber 27 and a lower chamber 26. Openings 81 are provided in plate 75, rim 64, and sample holder 9 to allow flow of fluid contained in lower chamber 26. A fill port 36 is provided in separator 34 to allow flow of fluid into lower chamber 26 and to allow pressure equalization between upper chamber 27 and lower chamber 26.

A pump (not shown) or other pressurizing device is used to completely fill upper chamber 27 with a pressurizing fluid through port 46. Pressure control pumps, gauges and related devices for introducing, monitoring and controlling fluid flow and pressure may be used to control pressure in testing cell 12. A thermal device (not shown) may be used to heat and/or cool the testing cell 12 during the testing process. The thermal device may be used in conjunction with a thermocouple or other temperature measurement device. The pressurizing, monitoring and control devices and/or the thermal device and temperature measurement device may be coupled to a processor or computer for monitoring and control.

Displacement sensor system 14 is positioned above the material expansion and shrinkage cell 12. Displacement sensor system 14 includes a transmitter 61 for transmitting a directed electromagnetic radiation 58 through opening bore 50, lens 48, and upper chamber 27. Electromagnetic radiation 58 strikes reflective upper surface 33 of transfer stand 8. Displacement sensor system 14 includes a sensor 63 to receive the reflected radiation 60 from the reflective upper surface 33 of transfer stand 8. In an exemplary embodiment, upper surface 33 of transfer stand 8 is constructed with a highly reflective surface, such as polished steel, to enhance reflection of electromagnetic radiation signal.

With sensor system 14 placed above cell 12 and transfer stand 8 positioned above sample 99, expansion of sample 99 pushes transfer stand 8 and reflective surface 33 upward. If sample 99 contracts, gravity pulls transfer stand 8 and surface 33 downward coincident with such contraction.

In an exemplary embodiment, the directed electromagnetic radiation 58 is a laser electromagnetic radiation, and the displacement sensor system 14 is a charge-coupled device (CCD) laser displacement sensor constructed to generate electromagnetic radiation 58 and to sense reflected radiation 60. A displacement sensor system 14 (i.e., CCD laser displacement sensor) is commercially available. An exemplary displacement sensor system 14 is a Keyence® model LK-G407 CCD laser displacement sensor. Keyence® is a registered trademark of Keyence Corporation. In operation, displacement sensor system 14 generates a directed electromagnetic radiation 58 and utilizes a sensor 63 to detect and sense reflected radiation 60. This results in a frictionless measurement system.

In an exemplary embodiment, transmitter, transmitter 61 and sensor 63 are fixedly placed a known distance apart in displacement sensor 14, and arranged to be generally parallel to surface 33. As surface 33 moves toward and away from transmitter 61 and sensor 63 the angle of received radiation 58 reflected from surface 33 changes. The distance between surface 33 and transmitter may thus be calculated using known methods.

Displacement sensor system 14 provides output to a processor or computer (not shown) through commercially available input-output connections, wired or wireless connections, etc. The processor may record and process measurements made by the displacement sensor system 14 as a function of time and may be programmed or include software or code to perform calculations and generate information relating to data obtained, such data including, for example, linear displacement of surface 33 and calculated volume variations as a function of time.

Operation

To test a material sample with instrument cell apparatus 10, lower plug 24 is initially removed from the cell body 22. The transfer stand 8 is then removed from sample holder 9. A material sample 99 is placed in sample holder 9 and the transfer stand 8 slidably inserted into the sample holder 9 so that material sample 99 is positioned between flange 35 and plate 75. Lower plug 24 is attached to cell body 22 with separator 34 positioned on sample holder 9 shoulder 76. Upon assembly, separator 34 extends between sample holder 9 and cell body 22. Transfer stand 8 head 11 is positioned within sample holder 9 with head 11 slidably positioned proximate upper end 68 of sample holder 9.

Lower chamber 26 is filled with a sample fluid (not shown), through fill port 36. Upper chamber 27 is partially filled with a pressurizing fluid. Upper plug 42 is attached to the cell body 22. Fill port 36 allows equalization of fluid pressure between upper chamber 27 and lower chamber 26. In an exemplary embodiment, the sample fluid may be a drilling fluid. Pressurizing fluid may be water or other fluid that allows transmission of directed or reflected electromagnetic radiation. Other pressurizing fluid may be used if compatible with electromagnetic radiation 58 transmission therethrough. Stirrer 37 allows the sample fluid (not shown) in lower chamber 26 to be stirred and circulated within lower chamber 26. Temperature and pressure at a determined level may be applied, monitored and controlled by the apparatus 10.

As sample 99 cures or reacts to conditions in test cell 12, any volumetric change will displace flange 35 of transfer stand 8, which rests on sample 99. Displacement sensor system 14 is used to measure the linear displacement of transfer stand 8. Displacement sensor system 14 transmits directed electromagnetic radiation 58 from transmitter 61 on its lower surface 64. Electromagnetic radiation 58 passes through bore 50, lens 48, and pressurizing fluid in chamber 27, and strikes upper surface 33 of transfer stand 8. Radiation 60 is reflected from upper reflective surface 33. Radiation 60 passes through pressurizing fluid in upper chamber 27, lens 48, and bore 50, and strikes sensor 63 of displacement sensor system 14. Source electromagnetic radiation 58 may be generated substantially continuously or intermittently.

Displacement sensor system 14 relies on the determined distance 62 between transmitter 61 and the sensor 63 and triangulation calculations to compute the distance between displacement sensor system 14 and upper surface 33 of transfer stand 8.

A base reading is obtained identifying the initial distance between system sensor system 14 and upper surface 33 of transfer stand 8. As sample 99 expands or contracts, transfer stand 8 is displaced upwardly or downwardly. Displacement of transfer stand 8 correlates with relative expansion or shrinkage of the material sample 99 in sample holder 9.

Displacement sensor system 14 may be coupled to a processor (e.g., a computer, server, laptop, etc.) to record the measured displacement values and/or make desired calculations. The processor and software code or logic stored in memory may utilize displacement measurements to calculate the expansion and/or contraction of the sample and display the change in volume as a function of time.

In an exemplary embodiment, the initial distance between lower surface 45 of lens 48 and upper surface 33 of transfer stand 8 may be determined by triangulation.

Figure 2:
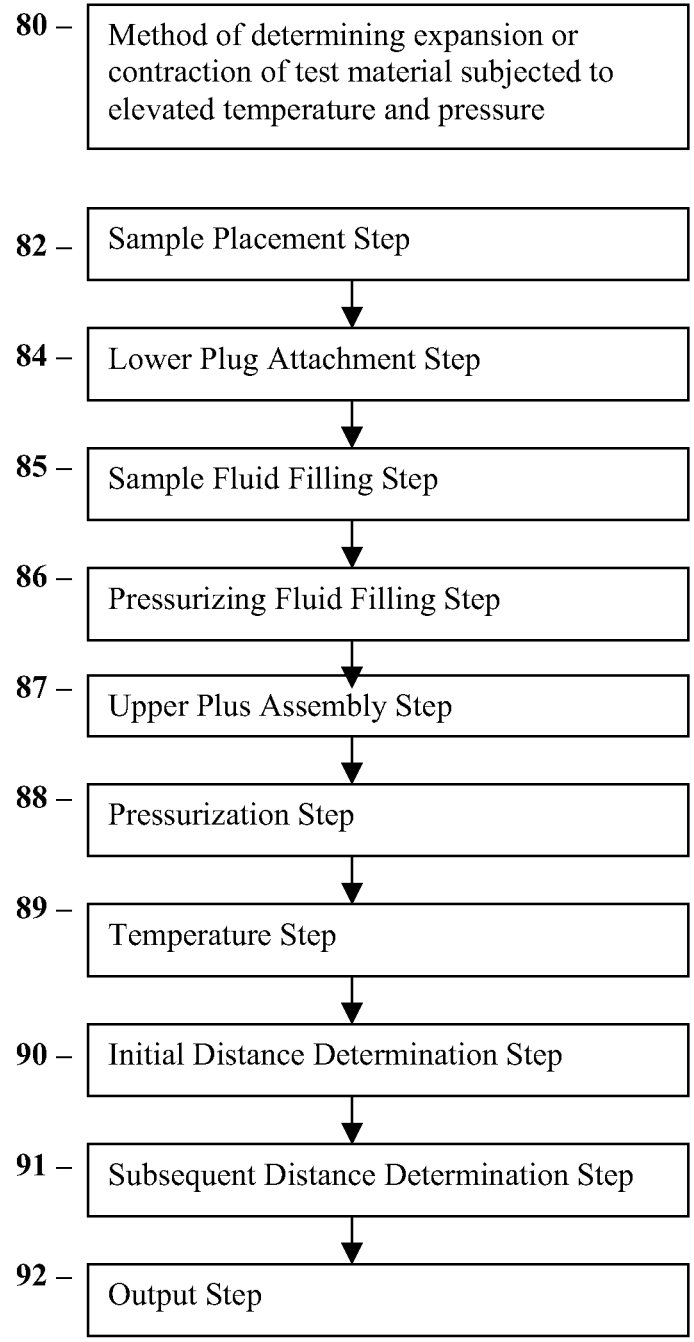
FIG. 2 is a block diagram of a method for testing a material in the cell of FIG. 1.

FIG. 2 illustrates a method 80 of determining expansion or contraction of a sample 99 subjected to determined temperature and pressure in test cell 12.

A sample placement step 82 involves placement of a sample 99 in sample holder 9 proximate a lower plug 24 of cell body 22 with a flange 35 of transfer stand 8 placed on sample 99.

A lower plug attachment step 84 comprises attaching lower plug 24 to cell body 22.

A sample fluid filling step 85 comprises filling lower chamber 26 with a sample fluid.

A pressurizing fluid filling step 86 comprises filling upper chamber 27 with a pressurizing fluid.

An upper plug assembly step 87 comprises attaching upper plug 42 to cell body 22.

A pressurization step 88 comprises pressurizing the test cell 12 to a determined pressure. Pressurization step 88 may be eliminated in an alternate embodiment wherein ambient pressure is a test condition. Pressurizing fluid filling step 86 may be eliminated in an embodiment wherein pressurization step 88 comprises both step 86 and step 88.

A temperature step 89 comprises applying a thermal device to test cell 12 to a determined temperature. Temperature step 89 may be eliminated in an alternate embodiment wherein ambient temperature is a test condition.

An initial determination step 90 comprises determining an initial location determination of upper surface 33 of transfer stand 8 utilizing a displacement sensor system 14 to measure the initial position of transfer stand upper surface 33.

A subsequent determination step 91 comprises determining a subsequent location of upper surface 33 of transfer stand 8 utilizing a displacement sensor system 14 to measure a subsequent position of transfer stand upper surface 33.

A series of subsequent determination steps 91 may be conducted over time to measure subsequent positions of transfer stand upper surface 33.

An output step 92 comprises providing data obtained to a processor (not shown).

Pressure and temperature measurement steps may be during the foregoing steps to monitor pressure and temperature during some or all of the foregoing steps. Pressurizing steps may be conducted from time to time to increase or decrease pressure within the test cell 12. Temperature steps may be conducted from time to time to adjust temperature within the test cell 12.

In an exemplary application of the method of the present invention, a plurality of apparatuses 10 may be used to determine the effectiveness of various compositions used to control expansion or contraction of a test sample. A plurality of apparatuses 10 may be provided with a test sample 99. A plurality of sample fluids may be used, each sample fluid having varying compositions or varying concentrations of compositions. The calculated volume change of each sample may be determined in each apparatus over time to allow comparison of the effectiveness of the various compositions in decreasing or increasing sample 99 volume under determined temperature and pressure conditions.

Figure 4:
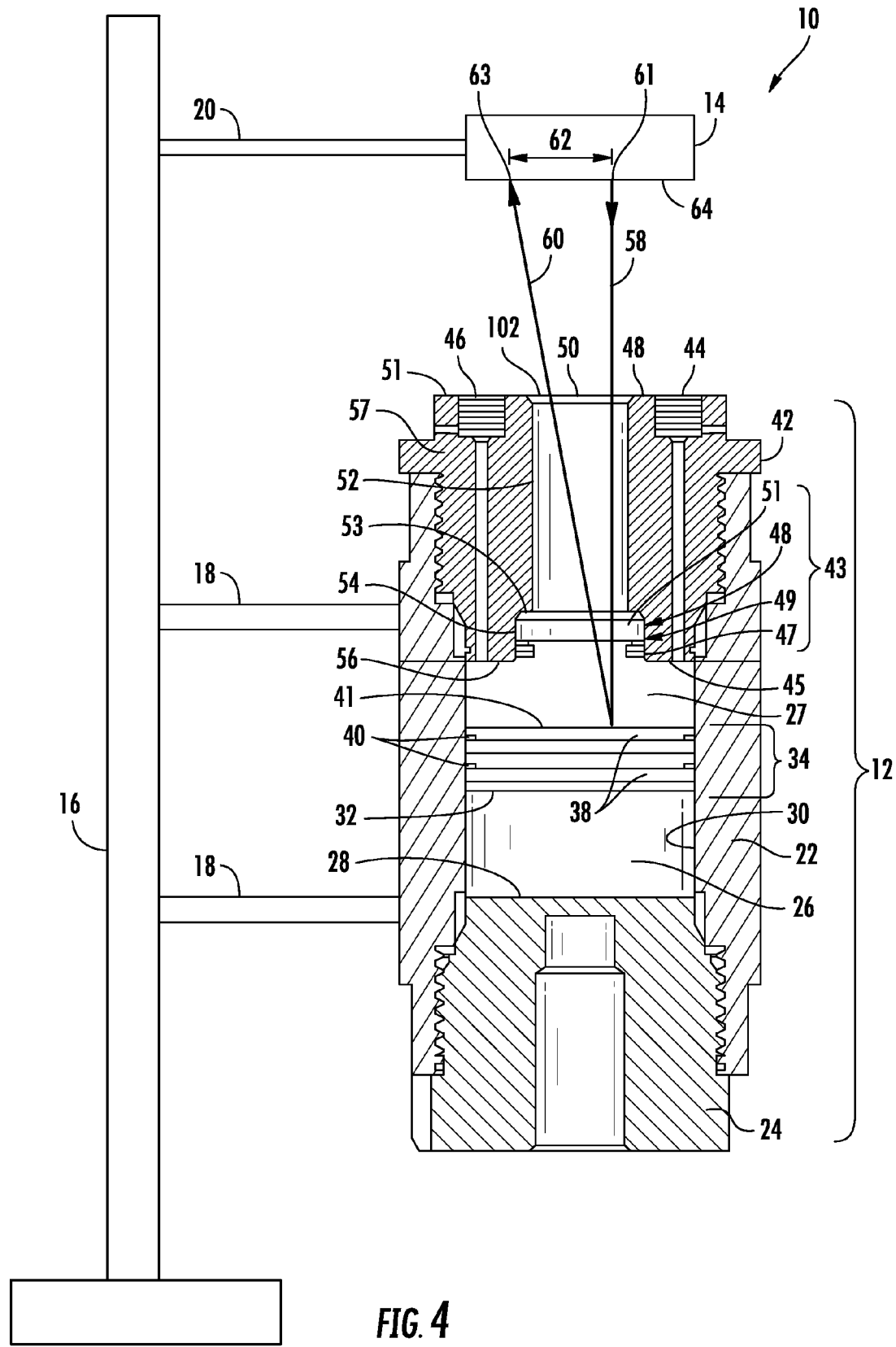
FIG. 4 is a partial cross-sectional view of an alternative embodiment for measuring expansion and contraction of a fluid.

Referring to FIG. 4, an alternative embodiment is depicted. In the alternative embodiment of FIG. 4 separator 34 sealingly separates upper chamber 27 from lower chamber 26. The embodiment of FIG. 4 provides for measurement of volume change of a fluid contained in lower chamber 26.

In the embodiment of FIG. 4, separator 34 comprises a circular disk having two annular grooves 40 around its periphery. O-rings 38 are inserted at least partially within annular groves 40. O-rings 38 comprise a slidable seal between separator 34 and inner wall 30. Separator 34 has a lower surface 32 and an upper surface 41.

Upper plug 42 includes a center bore 50, two high-pressure ports 44 and 46, and a lens assembly 43. Center bore 50 includes a small diameter upper section 52 and a large diameter lower open section 54. A shoulder 53 is created around the periphery of bore center 50 where small diameter upper section 52 meets large diameter lower open section 54.

Lens assembly 43 fits within large diameter lower open section 54 of center bore 50. Lens assembly 43 abuts shoulder 53 and a high-pressure seal is created between lens assembly 43 and the interior surface of center bore 50. Lens assembly 43 includes an o-ring 51, a lens 48, a spacer 49, and a lock ring 47. Lens 43 has a lower surface 45.

Referring to FIG. 4, a lower chamber 26 is formed by the upper surface 28 of lower plug 24, the lower surface 32 of separator 34, and the inner wall 30 of cell body 22. An upper chamber 27 is formed by the upper surface 41 of separator 34, the lower surface 56 of upper plug 42, which includes the lower surface 45 of lens 48, and the inner wall 30 of cell body 22.

In an exemplary embodiment, the directed electromagnetic radiation displacement sensor system 14 is connected to a processor (not shown). The processor may record measurements made by displacement sensor system 14 and may use the measurements to compute expansion and/or contraction of a sample fluid.

A pump (not shown) or other pressurizing device is used to completely fill upper chamber 27 with a pressurizing fluid through port 46. Gauges and related devices for introducing, monitoring and controlling desired pressure may be utilized to control pressure in upper chamber 27. A thermal device (not shown) may be used to heat and/or cool the material expansion and shrinkage cell 12. The thermal device may be used in conjunction with a thermocouple or other temperature measurement device. The pressurizing, monitoring and control devices and/or the thermal device and temperature measurement device may be coupled to a processor or computer for monitoring and control.

Referring to FIG. 4, the directed electromagnetic radiation displacement sensor system 14 is positioned above expansion and shrinkage cell 12 so that directed electromagnetic radiation 58 transmitted from sensor system 14 may travel through bore 50, lens 48, and upper chamber 27 and its contents, and impinge upper surface 41 of separator 34. Electromagnetic radiation displacement sensor system 14 is positioned so that it can sense reflected electromagnetic radiation 60. In an exemplary embodiment, the directed electromagnetic radiation displacement sensor system 14 may be a CCD laser displacement sensor.

In operation of the embodiment of FIG. 4, upper plug 42 is removed from cell body 22

Lower chamber 26 is filled with a sample fluid (not shown), separator 34 is positioned in its initial position, and upper plug 42 is attached to cell body 22.

A Pump (not shown) is used to fill upper chamber 27 with a pressurizing fluid (not shown). In an exemplary embodiment the pressurizing fluid is water. In alternative embodiments the pressurizing fluid may be other fluids as known in the art. The fluid should be compatible with the use of directed electromagnetic radiation 58 from an electromagnetic radiation displacement sensor system 14. The pump (not shown) is used to pressurize the pressurizing fluid.

The pressurizing fluid exerts a force on separator 34. Separator 34 in turn exerts a force on the sample fluid (not shown) in lower chamber 26, thereby pressurizing the sample fluid in lower chamber 26 to a desired pressure. Pressure in upper chamber 27 may be controlled by the pump, which pumps the pressurizing fluid into the upper chamber 27 as desired.

By controlling the pressure in upper chamber 27 the pressure on the sample fluid may be controlled. For example, it may be desired to maintain a constant pressure on the sample fluid in lower chamber 26. If the fluid sample expands as in reaction to conditions in the test cell 12, separator 34 will slide upward reducing the size of upper chamber 27. To maintain a constant pressure in upper chamber 27, the pressurizing fluid may be allowed to flow from upper chamber 27. If the pressure in upper chamber 27 is maintained constant, the pressure exerted on the sample fluid by separator 34 will remain constant, and therefore, the pressure in lower chamber 26 will remain constant. Alternatively, if the sample fluid contracts, the pump (not shown) may be used to add pressurizing fluid to upper chamber 27 in order to maintain constant pressure in upper chamber 27 and lower chamber 26. The pump may be connected to a computer or other controller for the purpose of control.

The directed electromagnetic radiation displacement sensor system 14 is used to measure displacement of separator 34. Sensor system 14 measures distance and change in distance from sensor system 14 to the upper surface 41 of separator 34.

In an exemplary embodiment sensor system 14 transmits directed electromagnetic radiation 58 from a transmitter 61 on its lower surface 64. Electromagnetic radiation 58 passes through bore 50, lens 48, and pressurizing fluid in chamber 27 and impinges reflective upper surface 41 of separator 34. Reflect electromagnetic radiation 60 passes through the pressurizing media in chamber 27, lens 48, and bore 50. Sensor 63 is positioned on the lower surface of electromagnetic radiation displacement sensor system 14 and senses the reflected electromagnetic radiation 60

Displacement sensor system 14 relies on the known distance 62 between transmitter 61 and the sensor 63 to compute the distance between displacement sensor system 14 and reflective upper surface 41 by triangulation.

Sensor system 14 may determine the distance between sensor system 14 and upper surface 41 of separator 34 continuously or at selected intervals. Expansion or contraction of fluid sample in lower chamber 26 results in upward or downward displacement of separator 34. The distances or differential distances determined by directed electromagnetic radiation displacement sensor system 14 throughout may be used to compute the displacement of separator 34 during the process. The displacement of separator 34 may be used in combination with the physical parameters of fluid sample expansion and shrinkage cell 12 to compute the percent expansion or contraction of the sample fluid in chamber 26.

Directed electromagnetic radiation displacement sensor system 14 may be connected to a processor to record the measured displacement values and/or make desired calculations. Software may utilize cell dimensions and the displacement measurements to calculate the expansion and/or contraction of the fluid sample and display the volume change as a function of time. Directed electromagnetic radiation displacement sensor system 14 may be calibrated to yield a zero value when separator 34 is in the initial position.

An apparatus 10 may be used sequentially in a plurality of tests to determine effectiveness of the various compositions.

In an alternative embodiment an acoustical displacement sensor (not shown) may be used instead of electromagnetic radiation displacement sensor system 14. In an alternative embodiment an induction displacement sensor (not shown) may be used instead of electromagnetic radiation displacement sensor system 14.

In an alternative embodiment of the apparatus of FIG. 4, separator 34 may be a flexible diaphragm. Cell body 22, lower plug 24, and/or upper plug 42 may be formed to receive the diaphragm as is known by those having skill in the art.

The apparatus and method of the present invention determines distance from the displacement sensor system 14 to reflective surface 33. Such distance information determined over time determines expansion or contraction of sample 99 as a function of time. Other measurable information regarding sample 99 is used in connection with the distance information to determine calculated volume expansion or contraction. Such calculations are readily performed or programmed by those skilled in the art.

One having skill in the art will understand that apparatus 10 may be used to test materials other than cement for expansion and/or shrinkage under controlled temperature and/or pressure conditions. Various embodiments of the invention will be understood from the foregoing description, and it will be apparent that, although embodiments of the invention have been described in detail, various changes, substitutions, and alterations may be made in the manner, procedure and/or details thereof without departing from the spirit and scope of the invention or sacrificing any of its material advantages, the forms hereinbefore described being merely exemplary embodiments thereof.

The depicted exemplary embodiments may be altered in a number of ways while retaining the inventive aspect, including ways not specifically disclosed herein.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features and characteristics described in conjunction with a particular aspect, embodiment or example of the invention are to be understood to be applicable to any other aspect, embodiment or example described herein unless incompatible therewith.

All of the features disclosed in this specification (including any accompanying claims, abstract and drawings), and/or all of the steps of any method or process so disclosed, may be combined in any combination, except combinations where at least some of such features and/or steps are mutually exclusive. In other words, the method steps have not been provided for in any particular sequential order and may be rearranged as needed or desired, with some steps repeated sequentially or at other times, during use.

Each feature disclosed in this specification (including any accompanying claims, abstract and drawings), may be replaced by alternative features serving the same, equivalent, or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

We claim:

1. A test cell for determining expansion or contraction of a sample, said test cell comprising:
    a test cell body;
    a reflective surface within said test cell body;
    said reflective surface moveable within said test cell body;
    a displacement sensor system;
    said displacement sensor system comprising a directed electromagnetic radiation transmitter and an electromagnetic radiation sensor; and
    said transmitter, said reflective surface and said sensor constructed and positioned to allow directed electromagnetic radiation from said transmitter to be transmitted toward said reflective surface and to allow electromagnetic radiation to be reflected from said reflective surface toward said sensor;
    wherein said displacement sensor system is adapted to utilize transmitted and reflected electromagnetic radiation to sense and quantify movement of said reflective surface and thereby sense and quantify expansion and/or contraction of said sample.

2. A test cell according to claim 1 wherein:
said displacement sensor system is exterior of said cell body;
a lens is provided in said test cell intermediate said reflective surface and said displacement sensor system; and
said lens is constructed to allow transmittal of electromagnetic radiation therethrough.

3. A test cell according to claim 2 wherein:
at least one test cell plug is attachable to said cell body; and
said lens is provided in said at least one test cell plug.

4. A test cell according to claim 3 wherein:
a sample holder is provided in said cell;
a transfer stand is received in said sample holder;
said reflective surface is attached to said transfer stand; and
said transfer stand is constructed to be moveable responsive to expansion or contraction of a sample contained in said sample holder.

5. A test cell according to claim 4 wherein:
said test cell comprises a hollow cylindrical body;
an upper plug is sealingly engaging said cylindrical body;
a lower plug is sealingly engaging said cylindrical body;
said lens is provided in said upper plug; and
said displacement sensor system is placed above said upper plug.

6. A test cell according to claim 5 wherein:
a separator is provided in said cell body;
said separator defines a lower chamber and an upper chamber within said cell body;
said sample holder is positioned in said lower chamber; and
said transfer stand is positioned at least partially in said lower chamber.

7. A test cell according to claim 6 wherein:
said transfer stand has a transfer stand head; and
said reflective surface comprises an upper surface of said transfer stand head.

8. A test cell according to claim 7 further comprising:
said lower chamber operable to receive a sample fluid;
said upper chamber operable to receive a pressurizing fluid;
a pressurizing device;
at least one temperature control device;
at least one temperature sensor; and
at least one pressure sensor.

9. A test cell according to claim 8 wherein:
a processor is connected to said displacement sensor system;
said processor receives data from said displacement sensor system; and
said processor provides expansion and contraction data through an output device.

10. A test cell according to claim 3 wherein:
said lens is held within a lens assembly; and
said lens assembly is sealingly positioned in said test cell plug.

11. A test cell according to claim 3 wherein said lens comprises a glass material.

12. A test cell according to claim 3 wherein said lens comprises a sapphire material.

13. A method of determining expansion or contraction of a sample in a test cell with a displacement sensor system comprising:
a sample placement step comprising placing a sample in a test cell proximate a transfer stand, said transfer stand connected to a reflective surface;
an initial determination step comprising determining the distance between the displacement sensor system and said reflective surface;
said initial determination step further comprising transmitting directed electromagnetic radiation from a transmitter in said displacement sensor system toward said reflective surface through a lens provided in said test cell;
said initial determination step further comprising sensing reflected electromagnetic radiation from said reflective surface by a sensor of said displacement sensor system;
at least one subsequent determination step comprising determining the distance between the displacement sensor system and said reflective surface;
said at least one subsequent determination step further comprising transmitting directed electromagnetic radiation from a transmitter in said displacement sensor system toward said reflective surface through a lens provided in said test cell; and
said at least one subsequent determination step further comprising sensing reflected electromagnetic radiation from said reflective surface by a sensor of said displacement sensor system;
wherein each said subsequent determination step utilizes said sensing reflected electromagnetic radiation from said reflective surface to sense and quantify movement of said reflective surface and thereby sense and quantify expansion and/or contraction of said sample.

14. The method of claim 13 further comprising:
multiple subsequent determination steps conducted over time.

15. The method of claim 14 further comprising:
processing distance information obtained from said initial determination and each said multiple determination step to determine distance between said displacement sensor system and said reflective surface as a function of time.

16. A test cell for determining expansion or contraction of a fluid sample, said test cell comprising:
a test cell body;
a reflective surface within said test cell body;
said reflective surface moveable within said test cell body;
a displacement sensor system;
said displacement sensor system comprising a directed electromagnetic radiation transmitter and an electromagnetic radiation sensor; and
said transmitter, said reflective surface and said sensor constructed and positioned to allow directed electromagnetic radiation from said transmitter to be transmitted toward said reflective surface and to allow electromagnetic radiation to be reflected from said reflective surface toward said sensor;
wherein said displacement sensor system is adapted to utilize transmitted and reflected electromagnetic radiation to sense and quantify movement of said reflective surface and thereby sense and quantify expansion and/or contraction of said fluid sample.

17. A test cell according to claim 16 wherein:
said displacement sensor system is exterior of said cell body;
a lens is provided in said test cell intermediate said reflective surface and said displacement sensor system;
said lens is constructed to allow transmittal of electromagnetic radiation therethrough;
at least one test cell plug is attachable to said cell body; and
said lens is provided in said at least one test cell plug.

18. A test cell according to claim 17 wherein:
a separator is provided in said cell body;
said separator defines a lower chamber and an upper chamber within said cell body;

said lower chamber is constructed to be operable to receive a fluid sample; and said upper chamber is constructed to be operable to receive a pressurizing fluid.

19. A test cell according to claim 18 wherein:

said separator is constructed to be moveable within said cell body responsive to expansion and contraction of a fluid sample; and said reflective surface is attached to said separator.

20. A test cell according to claim 19 further comprising:

a pressurizing device;

at least one temperature device;

at least one temperature sensor;

at least one pressure sensor;

a processor connected to said displacement sensor system;

said processor receiving data from said displacement sensor system; and said processor providing expansion and contraction data through an output device.

\* \* \* \* \*